US007811587B2

(12) United States Patent
Donovan

(10) Patent No.: US 7,811,587 B2
(45) Date of Patent: *Oct. 12, 2010

(54) BOTULINUM TOXIN THERAPY FOR NEUROPSYCHIATRIC DISORDERS

(75) Inventor: Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/749,461

(22) Filed: May 16, 2007

(65) Prior Publication Data

US 2007/0218085 A1    Sep. 20, 2007

Related U.S. Application Data

(63) Continuation of application No. 10/806,972, filed on Mar. 22, 2004, now Pat. No. 7,229,626, which is a continuation of application No. 10/143,078, filed on May 10, 2002, now Pat. No. 6,921,538.

(51) Int. Cl.
    *A61K 39/08* (2006.01)
(52) U.S. Cl. .................. 424/247.1; 424/184.1
(58) Field of Classification Search ........... None
    See application file for complete search history.

(56) References Cited

U.S. PATENT DOCUMENTS

| | | | | |
|---|---|---|---|---|
| 4,741,902 A * | 5/1988 | Haast ................ | 424/184.1 |
| 5,352,447 A | 10/1994 | Johnson ................ | 424/183.1 |
| 5,545,617 A | 8/1996 | Dartt et al. ................ | 514/12 |
| 5,549,884 A * | 8/1996 | Weinberger et al. ............ | 800/8 |
| 5,562,907 A | 10/1996 | Arnon ................ | 424/236.1 |
| 5,714,468 A * | 2/1998 | Binder ................ | 514/14 |
| 5,766,605 A | 6/1998 | Sanders et al. ............ | 424/239.1 |
| 5,843,971 A | 12/1998 | Boer et al. ................ | 514/365 |
| 5,989,545 A | 11/1999 | Foster et al. ............ | 424/183.1 |
| 6,113,915 A * | 9/2000 | Aoki et al. ................ | 424/236.1 |
| 6,203,794 B1 | 3/2001 | Dolly et al. ................ | 424/184.1 |
| 6,235,289 B1 | 5/2001 | Aoki ................ | 424/236.1 |
| 6,272,370 B1 | 8/2001 | Gilles et al. ................ | 600/411 |
| 6,290,961 B1 | 9/2001 | Aoki ................ | 424/184.1 |
| 6,306,403 B1 * | 10/2001 | Donovan ................ | 424/239.1 |
| 6,306,423 B1 * | 10/2001 | Donovan et al. ............ | 424/423 |
| 6,312,708 B1 | 11/2001 | Donovan ................ | 424/423 |
| 6,319,505 B1 | 11/2001 | Aoki ................ | 424/236.1 |
| 6,333,037 B1 | 12/2001 | Aoki ................ | 424/236.1 |
| 6,372,226 B2 | 4/2002 | Aoki ................ | 424/239.1 |
| 6,383,509 B1 * | 5/2002 | Donovan et al. ............ | 424/423 |
| 6,429,189 B1 | 8/2002 | Borodic ................ | 514/2 |
| 6,447,787 B1 | 9/2002 | Gassner et al. ............ | 424/247.1 |
| 6,451,544 B2 | 9/2002 | Giulian ................ | 435/7.2 |
| 6,458,365 B1 | 10/2002 | Aoki ................ | 424/239.1 |
| 6,464,986 B1 | 10/2002 | Aoki ................ | 424/239.1 |
| 6,475,745 B1 | 11/2002 | Giulian ................ | 435/7.2 |
| 6,506,399 B2 | 1/2003 | Donovan ................ | 424/423 |
| 6,524,580 B1 | 2/2003 | Donovan ................ | 424/94.5 |
| 6,545,126 B1 * | 4/2003 | Johnson et al. ............ | 530/350 |
| 6,585,970 B1 | 7/2003 | Donovan ................ | 424/94.5 |
| 6,585,993 B2 * | 7/2003 | Donovan et al. ............ | 424/423 |
| 6,620,415 B2 * | 9/2003 | Donovan ................ | 424/239.1 |
| 6,623,742 B2 | 9/2003 | Voet ................ | 424/236.1 |
| 6,645,496 B2 | 11/2003 | Aoki ................ | 424/184.1 |
| 6,645,500 B1 | 11/2003 | Halkier et al. ............ | 424/185.1 |
| 6,716,427 B1 | 4/2004 | Donovan ................ | 424/94.5 |
| 6,743,424 B1 | 6/2004 | Donovan ................ | 424/94.5 |
| 6,827,931 B1 * | 12/2004 | Donovan ................ | 424/94.63 |
| 6,921,538 B2 * | 7/2005 | Donovan ................ | 424/239.1 |
| 7,063,860 B2 * | 6/2006 | Chancellor et al. .......... | 424/450 |
| 7,270,287 B2 * | 9/2007 | First ................ | 424/239.1 |
| 7,357,934 B2 * | 4/2008 | Donovan et al. ......... | 424/239.1 |
| 2001/0036943 A1 * | 11/2001 | Coe et al. ................ | 514/220 |
| 2001/0053369 A1 * | 12/2001 | Donovan ................ | 424/239.1 |
| 2002/0192239 A1 * | 12/2002 | Borodic et al. ........... | 424/247.1 |
| 2003/0133951 A1 * | 7/2003 | Coe et al. ................ | 424/239.1 |
| 2003/0202990 A1 | 10/2003 | Donovan ................ | 424/239.1 |
| 2004/0018212 A1 | 1/2004 | Aoki ................ | 424/239.1 |
| 2004/0018213 A1 | 1/2004 | Aoki ................ | 424/239.1 |
| 2004/0062776 A1 | 4/2004 | Voet ................ | 424/239.1 |
| 2004/0146532 A1 * | 7/2004 | Gil et al. ................ | 424/239.1 |
| 2004/0213814 A1 * | 10/2004 | Ackerman ................ | 424/239.1 |
| 2005/0147626 A1 * | 7/2005 | Blumenfeld ............. | 424/239.1 |
| 2006/0083758 A1 * | 4/2006 | Dadas ................ | 424/239.1 |
| 2008/0003318 A1 * | 1/2008 | Aoki et al. ................ | 424/780 |

FOREIGN PATENT DOCUMENTS

| | | |
|---|---|---|
| DE | 10 150 415 A1 | 5/2003 |
| EP | 0 760 681 | 1/1999 |
| GB | 2228263 * | 8/1990 |
| WO | WO 99/55359 | 11/1999 |

OTHER PUBLICATIONS

Westra, I et al, Can. J. Ophthalmol, vol. 26(3), 1991, pp. 148-151, Occult pontine glioma in a patient with hemifacial spasm.*
O'Brien, Christopher F, MD, Injection Techniques for Botulinum Toxin using Electromyography and Electrical Stimulation, Muscle and Nerve, Supplement 6, 1997, pp. S176-S180.*
Micheli et al, reference of record.*
Auchus et al, (1995) reference of record.*
Murakami et al, 2001, British Journal of Pharmacology, vol. 134, pp. 507-520, Determination of effects of antiepileptic drugs on SNAREs-mediated hippocampal monoamine release using in vivo microdialysis.*

(Continued)

*Primary Examiner*—Robert B Mondesi
*Assistant Examiner*—Ginny Portner
(74) *Attorney, Agent, or Firm*—Kenton Abel; Claude Nassif; Debra Condino

(57) ABSTRACT

Methods for treating psychiatric disorders include intracranial administration of a therapeutically effective amount of a neurotoxin, such as a botulinum toxin type A, to a human patient.

19 Claims, No Drawings

OTHER PUBLICATIONS

Hainline, B, Psychiatr. Clin. North Am., Sep. 2005, vol. 28(3), pp. 713-735, Chronic pain: pysiological, diagostic, and management considerations. abstract only.*

Weintraub, Daniel et al, The Journal of Mangaed Care, vol. 14(2), pp. S59-S69, Parkinson's Diesease- Part 3: Neuropsychiatric symptoms.*

Bunevicius, R et al, Mood and anxiety disorders in women with treated hyperthyroidism and opthalmopathy caused by Grave's disease, General Hospital Psychiatry, vol. 27, 2005, pp. 133-139.* de Araujo Filho, G. M. et al, Epilepsy & Behavior, vol. 8, 2006, pp. 606-609 Neuropsychiatric profiles of patients with juvenile myoclonic epilepsy treated with valproate and topiramate.*

Auchus, AP et al., *Agitated behaviour relieved following treatment by vasodilators,* Neurology, Feb. 1995, vol. 45, No. 2, p. 393.

Baltazar, G., et al., European Journal of Cell Biology, Dec. 2000, vol. 79, No. 12, pp. 883-891.

Bassitt, D. Pastore, et al., Pharmacopsychiatry, Jul. 2000, vol. 33, No. 4, p. 155.

Bejjani, B., et al., *Bilateral subthalamic stimulation for Parkinson's disease by using three-dimensional sterotactic magnetic resonance imaging and electrophysiological guidance,* J Neurosurg, Apr. 2000, 92, pp. 615-625.

Bellezza, D. ,et al., *Stereostatic Interstitial Brachytherapy,* Text book of stereotactic and functional neurosurgery, McGraw-Hill, 1002, Chpt. 66, pp. 577-580.

Bigalke, H., et al., *Botulinum A neurotoxin inhibits non-cholinergic synaptic transmission in mouse spinal cord neurons in culture,* Brain Research, 360 (1985) 318-324.

Bigalke, H., et al., *Tetanus Toxin and botulinum a toxin inhibit release and uptake of various transmitters, as studied with particulate preparations from rat brain and spinal cord,* Naunyn-Schmiedeberg's Arch Pharmacol (1981) 316:244-251.

Bolay, H., et al., *Intrinsic brain activity triggers trigeminal meningeal afferents in a migraine model,* Nature Medicine, vol. 8, No. 2, Feb. 2002, pp. 136-142.

Brem, H., et al., *Placebo-controlled trial of saety and efficacy of intraoperative controlled delivery by biodegradable polymers of chemotherapy for recurrent gliomas,* The Lancet, vol. 345, Aprl 22, 1995, pp. 1008-1012.

Brem, H., et al., *The safety of interstitial chemotherapy with BCNU-loaded polymer follwed by radiation therapy in the treatment of newly diagnosed malignant gliomas: phase I trial,* J. of Neuro-Oncology 26:111-123, 1995.

Burn, David J., et al., *Use of Functional Imaging in Parkinsonism and Dementia,* Movement Disorders, 2003, vol. 18, Suppl 6, pp. S88-S95.

Burr Leiva, Daniel, *The neurochemistry of mania: a hypothesis of etiology and a rationale for treatment,* Prog. Neuro-Psychopharmacol & Biol. Psychiat. 1990, vol. 14, pp. 423-429.

Cereda, E., et al,. *Medicinal chemistry of muscarinic agonists for the treatment of dementia disorders,* Eur J Drug Metab Pharmacokinet, 1994 (3), pp. 179-183.

Clarke, P., et al., *Innervation of substantia nigra neurons by cholinergic afferents from pedunculopontine nucleus in the rat: neuroanatomical and electrophysiological evidence,* Neuroscience vol. 23, No. 3, pp. 1011-1019, 1987.

Coffield, et al., Eds: Jankovic, J., et al., *Therapy with Botulinum Toxin,* Marcel Dekker, Inc. 1994, p. 5.

Cosgrove, G. Rees, et al., *Cingulotomy in Psychosurgery,* Stereotactic and Functional Neurosurgery, 1998, P.L. Gildenberg, Eds., McGraw-Hill Pubs., Chpt. 203, pp. 1965-1979.

Cummings, J. L., et al., *Alzheimer's disease: cognitive and behavioral pharmacotherapy,* Connecticut Medicine, Sep. 1997, vol. 61, No. 9, pp. 543-552.

Duggan, Michael J., et al,. *A survey of botulinum neurotoxin substrate expression in cells,* Movement Disorders, 1005, May, 10(3), p. 376.

Egan, M.F., et al., Schizophrenia Bulletin, 1997, vol. 23, No. 4, pp. 583-609.

Fujimori, S., et al., *Neuropsychiatric disorders and GABA,* Nihon shinkei seishin yakurigaku zasshi, Japanese Journaql of Psychopharmacology, Oct. 2004, vol. 45, No. 5, pp. 265-271 (Abstract only).

Fung, L.K., et al., *Pharmacokinetics of Interstitial Delivery of Carmustine, 4-hydroperoxycyclophosphamide, and paclitaxel from a biodegradable polymer implant in the monkey brain,* Cancer Research, 58, 672-684, Feb. 15, 1998.

Garcia-Rill, E., et al., *Mesopontine neurons in schizophrenia,* Neuroscience vol. 66, No. 2, pp. 321-335, 1995.

Gaspar, L.E., et al., *Permanent Iodine implants for recurrent malignant gliomas,* Int. J. Radiation Onocology Biol. Phys., vol. 43, No. 5, pp. 977-982, 1999.

German, D.C., et al., *Mesopontine cholinergic and non-cholinergic neurons in schizophrenia,* Neuroscience, vol. 94, No. 1, pp. 33-38, 1999.

Gonelle-Gispert, C., et al., *SNAP-25a and—25b isofoms are both expressed in insulin-secreting cells and can function in insulin secretion,* Biochem. J. (1999) 339; pp. 159-165.

Habermann, E., et al., *Tetanus toxin and botulinum A and C neurotoxins inhibit noradrenaline release from cultured mouse brain,* J. Neurochemistry, 1988, pp. 522-527.

Habermann, E., *I-Labled Neurotoxin from Clostridium botulinum A: preparation, binding to synaptosomes and ascent to the spinal cord,* Naunyn-Schmiedeberg's Arch. Pharmacol. 281, 47-56 (1974).

Habermann, E., *Inhibition by tetanus and botulinum A toxin of the release of [$^3$ H]noradrenaline and [$^3$ H]GABA from rat brain homogenate,* Experientia 44 (1988) pp. 224-226.

Harrison' Principles of Internal Medicine, 1988, 14$^{th}$ Edition, McGraw-Hill , Table of Contents.

Hussain, E.S., et al., *A cohort study of psychosurgery cases from a defined population,* J. Neurol Neurosurg Psychiatry, Mar. 1998, vol. 51, No. 3, pp. 345-352.

Jimenez-Jimenez, F.J., et al., Drugs (New Zealand), 2001, vol. 61, No. 15, pp. 2207-2220.

Kim, C.H., et al., *Anterior cingulotomy for refractory obsessive-compulsive disorder,* Acta Psychiatr Scand., Apr. 2003, vol. 107, No. 4, pp. 283-290.

Kim, M.C., et al., *Review of long-term results of stereostatic psychosurgery,* Neurol Med Chri (Tokyo), Sep. 2002, vol. 42, No. 9, pp. 365-371.

Kurata, K., et al., Japanese Journal of Psychiatry and Neurology, Mar. 1993, vol. 47, No. 1, pp. 115-119.

Levy, M.L., et al., *Neuropsychiatric Symptons and Cholinergic Therapy for Alzheimer's Disease,* Gerontology, 1999;45(suppl 1)15-22.

Liberman, A., *Managing the neuropsychiatric symptoms of Parkinson's disease,* Neurology, Jun. 1998, vol. 50 (6 Suppl 6), pp. S33-S38.

Low, Phillip A., Current Opinion in Neurology, Oct. 2002, vol, 15, No. 5, pp. 605-609.

Marchese Ragona, R., et al. *Management of Parotid Sialocele with Botulinum Toxin,* The Laryngoscope 109, Aug. 1999, pp. 1344-1346.

Marjama-Lyons, J., et al., *Tremor-Predominant Parkinson's Disease,* Drugs & Aging Apr. 2000; 16(4); 273-278.

Medline Plus Encyclopedia: *Stress and Anxiety Definition,* provided by the US National library and The National Institute of Health, Aug. 6, 2007.

Meltzer, H., et al., *The dopamine hypothesis of schizophrenia: a review,* Schizophrenia Bulletin, vol. 2, No. 1, 1976, pp. 19-76.

Micheli, Federico, et al., *Hemifacial spasm triggered by vasodilators,* Clinical Neurology, 1998, vol. 21, No. 3, pp. 199-200.

Moyer, E., et al., *Botulinum Toxin Type B: Experimental and Clincal Experience,* Therapy with Botulinum Toxin 1994 , Chp. 6, pp. 71-85.

Naumann, M., et al., *Botulinum toxin type a in the treatment of focal, axillary and palmar hyperhidrosis and other hyperhidrotic conditions,* European Journal of Neurology 1999, 6 (suppl 4) S111-S115.

Nowinski, W.L., et al., *Computer-Aided stereotactic functional neurosurgery enhanced by the use of the multiple brain atlas database,* IEEE Transactions on Medical Imaging, vol. 19, No. 1, Jan. 2000, pp. 62-69.

Pahapill, P., et al., *Tremor arrest with thalamic microinjections of muscimol in patients with essential tremor*, Ann Neurol 1999;46:249-252.

Pearce, L.B., et al., *Pharmacologic characterization of botulinum toxin for basic science and medicine*, Toxicon 1997;35(9):1373-412.

Rapaport, A., et al., Mar. 2000, vol. 15, No. 2, Movement Disorders, pp. 352-355.

Sacco, K.A., et al., Journal of psychopharmacology, Dec. 2004, vol. 18, No. 4, pp. 457-474 (Abstract only).

Sanchez-Prieto, J., et al., *Botulinum toxin a blocks glutamate exocytosis from guinea-pig cerebral cortical synaptosomes*, Eur J. Biochem Jun. 1987; 165(3):675-81.

Sarter, M., et al., *Basal forebrain afferent projections modulating cortical acetylcholine, attention, and implications for neuropsychiatric disorders*, ANN NY Acad Sci 1999; 877:368-82.

Schantz, E.J., et al., *Properties and use of botulinum toxin and other microbial neurotoxins in medicine*, Microbiological Reviews Mar. 1992; vol. 56, No. 1; p. 80-99.

Scharfen, C.O., et al., *High activity iodine-125 interstitial implant for gliomas*, Int. J. Radiation Oncology Biol. Phys., vol. 24, 1992; pp. 583-591.

Shaari, et al., Eds: Jankovic, J., et al., *Therapy with Botulinum Toxin*, Marcel Dekker, Inc. 1994, p. 150.

Shabnam, Ghazi-Norri, et al., *Therapies for Depression in Parkinson's Disease*, Chochrane database of systematic reviews, 2003, vol. 3, Abstract only.

Singh, B., *Critical aspects of bacterial protein toxins*, Chapter 4, Natural Toxins II, Plenum Press (1996) pp. 63-84.

Sloop, R., et al., *Reconstituted botulinum toxin type A does not lose potentcy in humans if it is refrozen or refrigerated for 2 weeks before use*. Neurology 1997,48:249-253.

Sramka, M., et al., *Long-term results in patients with stereotaxic surgery for psychopathological disorders*, Bratisl. Lek. Listy, 1992, 93, 7, pp. 364-366 (English abstract enclosed).

Tandon, R., et al., *The cholinergic system in schizophrenia reconsidered: anticholinergic modulation of sleep and symptom profiles*, Neuropsychopharmacology 1999, vol. 21, No. S6 pp. S189-S202.

Teipel, S.J., et al., *In Vivo neuroreceptor imaging and applications for alzheimer's disease*, Drug News Perspect 12(6) Jul. 1999, pp. 341-350.

Thibaut, F. et al., *The dopamine transporter: characterization and physiopathologic implications*, L'Encephale (France, English abstract), Nov.-Dec. 1995, vol. 21, No. 6, pp. 445-451.

Velickovic, M., et al., Drugs (New Zealand), 2001, vol. 61, No. 13, pp. 1921-1943.

Weigand, H., et al., *I-Labelled Botulinum A Neurotoxin: pharmacokinetics in cats after intramuscular injection*, Naunyn-Schmiedeberg's Arc. Pharmacol. 292, 161-165 (1976).

Wheeler, Anthony H., *Therapeutic Uses of Botulinum Toxin*, American Family Physician, Feb. 1, 1997, vol. 55, No. 2, p. 541.

White, K.E., et al., *Schizophrenia and Alzheimer's Disease: clinical and pathophysiologic analogies*, Comprehensive Psychiatry, vol. 37, No. 3 (May/Jun.) 1996, pp. 188-195.

Yoshimura, D.M., et al., *Treatment of Hemifacial Spasm with Botulinum Toxin*, Muscle Nerve 1992, vol. 15, No. 9, pp. 1045-1049.

Yu, Y.L., et al., *Treatment of idiopathic hemifacial spasm with botulinum toxin*, Acta Neurol Scand, 1992, vol. 85. No. 1, pp. 55-57.

* cited by examiner

BOTULINUM TOXIN THERAPY FOR NEUROPSYCHIATRIC DISORDERS

CROSS REFERENCE

This application is a continuation of prior application Ser. No. 10/806,972, filed Mar. 22, 2004, which is a continuation of prior application Ser. No. 10/143,078, filed May 10, 2002, now U.S. Pat. No. 6,921,538, the disclosures of which are herby incorporated by reference in their entireties.

BACKGROUND

The present invention relates to methods for treating neuropsychiatric disorders. In particular, the present invention relates to methods for treating neuropsychiatric disorders by intracranial administration of a neurotoxin.

Neuropsychiatric Disorders

A neuropsychiatric disorder is a neurological disturbance that is typically labeled according to which of the four mental faculties are affected. For example, one group includes disorders of thinking and cognition, such as schizophrenia and delirium; a second group includes disorders of mood, such as affective disorders and anxiety; a third group includes disorders of social behavior, such as character defects and personality disorders; and a fourth group includes disorders of learning, memory, and intelligence, such as mental retardation and dementia. Accordingly, neuropsychiatric disorders encompass schizophrenia, delirium, Alzheimer's disease, depression, mania, attention deficit disorders, drug addiction, dementia, agitation, apathy, anxiety, psychoses, post-traumatic stress disorders, irritability, and disinhibition.

Schizophrenia

Schizophrenia is a disorder that affects about one percent of the world population. Three general symptoms of schizophrenia are often referred to as positive symptoms, negative symptoms, and disorganized symptoms. Positive symptoms may include delusions (abnormal beliefs), hallucinations (abnormal perceptions), and disorganized thinking. Hallucinations may be auditory, visual, olfactory, or tactile. Disorganized thinking may manifest itself in schizophrenic patients by disjointed speech and the inability to maintain logical thought processes. Negative symptoms may represent the absence of normal behavior. Negative symptoms include emotional flatness or lack of expression and may be characterized by social withdrawal, reduced energy, reduced motivation, and reduced activity. Catatonia may also be associated with negative symptoms of schizophrenia. The symptoms of schizophrenia should continuously persist for a duration of about six months in order for the patient to be diagnosed as schizophrenic. Based on the types of symptoms a patient reveals, schizophrenia may be categorized into subtypes including catatonic schizophrenia, paranoid schizophrenia, and disorganized schizophrenia.

The brains of schizophrenic patients are often characterized by enlarged lateral ventricles, which may be associated with a reduction of the hippocampus and an enhancement in the size of the basal ganglia. Schizophrenic patients may also have enlarged third ventricles and widening of sulci. These anatomical characterizations point to a reduction in cortical tissue.

Although the cause of schizophrenia is not precisely known, there are several hypotheses regarding the causes. One hypothesis is that schizophrenia is associated with increased dopamine activity within the cortical and limbic areas of the brain. This hypothesis is supported by the therapeutic effects achieved by antipsychotic drugs that block certain dopamine receptors. In addition, amphetamine use may be associated with schizophrenia-like psychotic symptoms; amphetamines act on dopamine receptors.

Examples of antipsychotic drugs that may be used to treat schizophrenic patients include phenothizines, such as chlorpromazine and trifluopromazine; thioxanthenes, such as chlorprothixene; fluphenazine; butyropenones, such as haloperidol; loxapine; mesoridazine; molindone; quetiapine; thiothixene; trifluoperazine; perphenazine; thioridazine; risperidone; dibenzodiazepines, such as clozapine; and olanzapine. Although these agents may relieve the symptoms of schizophrenia, their administration may also result in undesirable side effects including Parkinson's disease-like symptoms (tremor, muscle rigidity, loss of facial expression); dystonia; restlessness; tardive dyskinesia; weight gain; skin problems; dry mouth; constipation; blurred vision; drowsiness; slurred speech; agranulocytosis.

Antipsychotic drugs are believed to primarily act on dopamine receptors with a particular affinity for the $D_2$, $D_3$, and $D_4$ receptors. It is believed that the $D_3$ and $D_4$ receptors may have a higher affinity for certain antipsychotics, such as clozapine, as compared to the others. Brains of schizophrenic patients appear to have increased numbers of $D_2$ receptors in the caudate nucleus, the nucleus accumbens (ventral striatum), and the olfactory tubercule.

Dopamine neurons may be organized into four major subsystems: the tuberoinfundibular system; the nigrostriatal system; the mesolimbic system; and the mesocortical system. The tuberoinfundibular dopaminergic system originates in cell bodies of the arcuate nucleus of the hypothalamus and projects to the pituitary stalk. This system may be involved in secondary neuroendocrine abnormalities in schizophrenia. The nigrostriatal dopaminergic system originates in the substantia nigra and projects primarily to the putamen and the caudate nucleus. The mesolimbic dopaminergic system originates in the ventral tegmental area and projects to the mesial component of the limbic system, which includes the nucleus accumbens, the nuclei of the stria terminalis, parts of the amygdala and hippocampus, the lateral septal nuclei, and the mesial frontal, anterior cingulate, and entorhinal cortex. The nucleus accumbens is a convergence site from the amygdala, hippocampus, entorhinal area, anterior cingulate area, and parts of the temporal lobe. Thus, the mesolimbic dopaminergic projection may modulate and transform information conveyed from the nucleus accumbens to the septum, hypothalamus, anterior cingulate area, and frontal lobes, and overactive modulation of the nucleus accumbens output to these areas may contribute to positive symptoms associated with schizophrenia. The mesocortical dopaminergic system originates in the ventral tegmental area and projects to the neocortex and heavily to the prefrontal cortex. This component may be important in the negative symptoms of schizophrenia.

The ventral tegmental area, which is the source of origination of the dopaminergic input to the nucleus accumbens, receives a cholinergic input from the pedunculopontine nuclei of the brainstem. The pedunculopontine nucleus provides an excitatory cholinergic input to the ventral tegmental area (Clarke et al., *Innervation of substantia nigra neurons by cholinergic afferents from the pedunculopontine nucleus in the rat. Neuroanatomical and electrophysiological evidence,* Neuroscience, 23:1011-1019, 1987). It has been reported that schizophrenic patients have an increased number of cholinergic neurons in the pedunculopontine nuclei (Garcia-Rill et al., *Mesopontine neurons in schizophrenia,* Neuroscience, 66(2):321-335, 1995). However, these results were not confirmed in one study (German et al., *Mesopontine cholinergic and non-cholinergic neurons in schizophrenia*, Neuroscience, 94(1):33-38, 1999).

Mania

Mania is a sustained form of euphoria that affects millions of people in the United States who suffer from depression. Manic episodes may be characterized by an elevated, expansive, or irritable mood lasting several days, and is often accompanied by other symptoms, such as, overactivity, overtalkativeness, social intrusiveness, increased energy, pressure of ideas, grandiosity, distractibility, decreased need for sleep, and recklessness. Manic patients may also experience delusions and hallucinations.

Depressive disorders may involve serotonergic and noradrenergic neuronal systems based on current therapeutic regimes that target serotonin and noradrenalin receptors. Serotonergic pathways originate from the raphe nuclei of the brain stem, and noradrenergic pathways originate from the locus ceruleus. Decreasing the electrical activity of neurons in the locus ceruleus may be associated with the effects mediated by depression medications.

Mania likely results from an imbalance in the chemical messengers within the brain. It has been proposed that mania may be attributed to a decline in acetylcholine. A decline in acetylcholine may result in a relatively greater level of norepinephrine. Administering phosphotidyl choline has been reported to alleviate the symptoms of mania.

Anxiety

Anxiety disorders may affect between approximately ten to thirty percent of the population, and may be characterized by frequent occurrence of symptoms of fear including arousal, restlessness, heightened responsiveness, sweating, racing heart, increased blood pressure, dry mouth, a desire to run or escape, and avoidance behavior. Generalized anxiety persists for several months, and is associated with motor tension (trembling, twitching, muscle aches, restlessness); autonomic hyperactivity (shortness of breath, palpitations, increased heart rate, sweating, cold hands), and vigilance and scanning (feeling on edge, exaggerated startle response, difficult in concentrating).

Benzodiazepines, which enhance the inhibitory effects of the gamma aminobutyric acid (GABA) type A receptor, are frequently used to treat anxiety. Buspirone is another effective anxiety treatment.

Alzheimer's Disease

Alzheimer's disease is a degenerative brain disorder characterized by cognitive and noncognitive neuropsychiatric symptoms, which accounts for approximately 60% of all cases of dementia for patients over 65 years old. Psychiatric symptoms are common in Alzheimer's disease, with psychosis (hallucinations and delusions) present in approximately fifty percent of affected patients. Similar to schizophrenia, positive psychotic symptoms are common in Alzheimer's disease. Delusions typically occur more frequently than hallucinations. Alzheimer's patients may also exhibit negative symptoms, such as disengagement, apathy, diminished emotional responsiveness, loss of volition, and decreased initiative.

Alzheimer's disease patients may also exhibit enlargement of both lateral and third ventricles as well as atrophy of temporal structures.

It is possible that the psychotic symptoms of Alzheimer's disease may involve a shift in the concentration of dopamine or acetylcholine, which may augment a dopaminergic/cholinergic balance, thereby resulting in psychotic behavior. For example, it has been proposed that an increased dopamine release may be responsible for the positive symptoms of schizophrenia. This may result in a positive disruption of the dopaminergic/cholinergic balance. In Alzheimer's disease, the reduction in cholinergic neurons effectively reduces acetylcholine release resulting in a negative disruption of the dopaminergic/cholinergic balance. Indeed, antipsychotic agents that are used to relieve psychosis of schizophrenia are also useful in alleviating psychosis in Alzheimer's patients.

Several of the symptoms associated with the neuropsychiatric disorders appear to be, at least in part, attributed to hyperexcitability of neurons within the brain. This interpretation is supported by the pharmacology associated with current therapeutic treatments. For example, many of the antipsychotic treatments are directed to interfering with binding of dopamine to dopamine receptors, as discussed above. Similarly, mania and anxiety are often treated with benzodiazepines, which enhance the inhibitory effects of GABA-mediated inhibition. U.S. Pat. No. 6,306,403 discloses intracranial administration of a botulinum toxin to treat various movement disorders. Additionally, it is known that stereotactic procedures can be used to administer a pharmaceutical to a discrete brain area to successfully alleviate a parkinsonian tremor. See e.g. Pahapill P. A., et al., *Tremor arrest with thalamic microinjections of muscimol in patients with essential tremor*, Ann Neur 46(2); 249-252 (1999).

However, current therapeutic treatments result in several adverse side-effects. These side-effects may be attributed to the fact that the pharmaceutical agents are typically administered systemically, and therefore, the agents have a relatively non-specific action with respect to the various biological systems of the patient. For example, administration of benzodiazepines may result in sedation and muscle relaxation. In addition, tolerance may develop to these drugs, as well as withdrawal seizures may develop. Current therapeutic strategies also require consistent and repeated administration of the agents to achieve the desired effects.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

[1] Available from Allergan, Inc. of Irvine, Calif. Under tradename BOTOX® in 100 unit vials)

Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type B: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_c$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond.

Botulinum toxins have been used in clinical settings for the treatment of neuromuscular disorders characterized by hyperactive skeletal muscles. A botulinum toxin type A complex has been approved by the U.S. Food and Drug Administration for the treatment of blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem, J* 1;339 (pt 1):159-65:1999, and *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by *Clostridial* bacterium as complexes comprising the 150 kD botulinum toxin protein molecule along with associated non-toxin proteins. Thus, the botulinum toxin type A complex can be produced by *Clostridial* bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus*

*Toxin and Botulinum A and C Neurotoxins Inhibit Noradrenaline Release From Cultured Mouse Brain*, J Neurochem 51(2);522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675-681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9);1373-1412 at 1393; Bigalke H., et al., *Botulinum A Neurotoxin Inhibits Non-Cholinergic Synaptic Transmission in Mouse Spinal Cord Neurons in Culture*, Brain Research 360;318-324:1985; Habermann E., *Inhibition by Tetanus and Botulinum A Toxin of the release of [$^3$H]Noradrenaline and [$^3$H]GABA From Rat Brain Homogenate*, Experientia 44;224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56;80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2\times10^8$ $LD_{50}$ U/mg or greater; purified botulinum toxin type B with an approximately 156 kD molecular weight with a specific potency of $1-2\times10^8$ $LD_{50}$ U/mg or greater, and; purified botulinum toxin type F with an approximately 155 kD molecular weight with a specific potency of $1-2\times10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo.

Pure botulinum toxin is so labile that it is generally not used to prepare a pharmaceutical composition. Furthermore, the botulinum toxin complexes, such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology,* 48:249-53:1997.

It has been reported that botulinum toxin type A has been used in clinical settings as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Jyons, J., et al., *Tremor-Predominant Parkinson's Disease,* Drugs & Aging 16(4);273-278:2000.

It is known that botulinum toxin type A can have an efficacy for up to 12 months (*European J. Neurology* 6(Supp 4):S111-S1150:1999), and in some circumstances for as long as 27 months. *The Laryngoscope* 109:1344-1346:1999. However, the usual duration of an intramuscular injection of Botox® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and Dysport® available from Beaufour Ipsen, Porton Down, England. A botulinum toxin type B preparation (MyoBloc®) is available from Elan Pharmaceuticals of San Francisco, Calif.

In addition to having pharmacologic actions at the peripheral location, botulinum toxins may also have inhibitory effects in the central nervous system. Work by Weigand et al, *Nauny-Schmiedeberg's Arch. Pharmacol.* 1976; 292, 161-165, and Habermann, *Nauny-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified *clostridial neurotoxin* or fragment thereof, preferably a botulinum toxin, chemically conjugated or recombinantly fused to a particular targeting moiety can be used to treat pain by administration of the agent to the spinal cord.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is a method for effectively treating a neuropsychiatric disorder by administration of a pharmaceutical which has the characteristics of long duration of activity, low rates of diffusion out of a chosen intracranial target tissue where administered, and nominal systemic effects at therapeutic dose levels.

SUMMARY

The present invention meets this need and provides methods for effectively treating neuropsychiatric disorders by intracranial administration of a neurotoxin which has the characteristics of long duration of activity, low rates of diffusion out of an intracranial site where administered and insignificant systemic effects at therapeutic dose levels.

The following definitions apply herein:

"About" means approximately or nearly and in the context of a numerical value or range set forth herein means ±10% of the numerical value or range recited or claimed.

"Local administration" means direct administration of a pharmaceutical at or to the vicinity of a site on or within an animal body, at which site a biological effect of the pharmaceutical is desired. Local administration excludes systemic routes of administration, such as intravenous or oral administration.

"Neurotoxin" means a biologically active molecule with a specific affinity for a neuronal cell surface receptor. Neurotoxin includes *Clostridial* toxins both as pure toxin and as complexed with one to more non-toxin, toxin associated proteins "Intracranial" means within the cranium or at or near the dorsal end of the spinal cord and includes the medulla, brain stem, pons, cerebellum and cerebrum.

Methods for treating neuropsychiatric disorders comprise the step of intracranially administering a neurotoxin to a patient. The neurotoxin is administered in a therapeutically effective amount to alleviate at least one symptom of the disorder. The neurotoxin alleviates the symptoms associated with the disorder by reducing secretions of neurotransmitter from the neurons exposed to the neurotoxin.

A suitable neurotoxin may be a neurotoxin made by a bacterium, for example, the neurotoxin may be made from a *Clostridium botulinum*, *Clostridium butyricum*, or *Clostridium beratti*. In certain embodiments of the invention, neuropsychiatric disorders are treated by intracranially administering a botulinum toxin to the patient. The botulinum toxin may be a botulinum toxin type A, type B, type $C_1$, type D, type E, type F, or type G. The botulinum toxin may be administered in an amount of between about $10^{-3}$ U/kg and about 10 U/kg. The effects of the botulinum toxin may persist for between about 1 month and 5 years.

Other neurotoxins include recombinantly produced neurotoxins, such as botulinum toxins produced by *E. coli*. In addition or alternatively, the neurotoxin can be a modified neurotoxin, that is a neurotoxin which has at least one of its amino acids deleted, modified or replaced, as compared to a native or the modified neurotoxin can be a recombinant produced neurotoxin or a derivative or fragment thereof. The neurotoxins are still able to inhibit neurotransmitter release.

The neurotoxin is administered to a site within the brain that is believed to be involved in the disorder being treated. The neurotoxin may be administered to a lower brain region, the pontine region, the pedunculopontine nucleus, the locus ceruleus, or the ventral tegmental area, for example. The neurotoxin may alleviate the symptom that is associated with hyperactive neurotransmitter release. The neurotoxin may also restore a balance between two neuronal systems to alleviate the disorder. The neurotoxin administered to the patient may inhibit acetylcholine release from cholinergic neurons, may inhibit dopamine release from dopaminergic neurons, may inhibit the release of norepinephrine from noradrenergic neurons.

The neuropsychiatric disorders treated in accordance with the methods disclosed herein include, and are not limited to, schizophrenia, Alzheimer's disease, mania, and anxiety. The neurotoxin can alleviate a positive symptom associated with the neuropsychiatric disorder, for example schizophrenia, and can alleviate the symptoms within a few hours after administration.

I have surprisingly found that a botulinum toxin, such as botulinum toxin type A, can be intracranially administered in amounts between about $10^{-4}$ U/kg and about 10 U/kg to alleviate a neuropsychiatric disorder experienced by a human patient. Preferably, the botulinum toxin used is intracranially administered in an amount of between about $10^{-3}$ U/kg and about 1 U/kg. Most preferably, the botulinum toxin is administered in an amount of between about 0.1 unit and about 5 units. Significantly, the neuropsychiatric disorder alleviating effect of the present disclosed methods can persist for between about 2 months to about 6 months when administration is of aqueous solution of the neurotoxin, and for up to about five years when the neurotoxin is administered as a controlled release implant.

Another preferred method within the scope of the present invention is a method for improving patient function, the method comprising the step of intracranially administering a neurotoxin to a patient, thereby improving patient function as determined by improvement in one or more of the factors of reduced pain, reduced time spent in bed, increased ambulation, healthier attitude and a more varied lifestyle.

DESCRIPTION

The present invention is based on the discovery that intracranial administration of a neurotoxin can provide significant and long lasting relief from a variety of different neuropsychiatric disorders. Intracranial administration permits a neurotoxin to be locally administered at a site, within a patient's cranium, that has a direct effect on the neurons involved in the disorders, and avoids complications associated with passage of the neurotoxin across the blood brain barrier. Thus, intracranial administration provides greater local dosages of a neurotoxin to a brain area than is achieved with systemic routes of administration, and avoids the non-specificity associated with systemic administration of current therapeutic agents. Indeed, systemic administration of a neurotoxin, such as a botulinum toxin, is contraindicated due to the severe complications (i.e. botulism) which can result from entry of a botulinum toxin into the patient's general circulation.

The neurotoxins used in accordance with the invention disclosed herein are neurotoxins that inhibit transmission of chemical or electrical signals between select neuronal groups that are involved in the neuropsychiatric disorders. The neurotoxins preferably are not cytotoxic to the cells that are exposed to the neurotoxin. The neurotoxin may inhibit neurotransmission by reducing or preventing exocytosis of neurotransmitter from the neurons exposed to the neurotoxin. Or, neurotoxins may reduce neurotransmission by inhibiting the generation of action potentials of the neurons exposed to the toxin. The suppressive effects provided by the neurotoxin should persist for a relatively long period of time, for example, for more than two months, and potentially for several years.

Examples of neurotoxins used to treat neuropsychiatric disorders, include, and are not limited to, neurotoxins made from *Clostridium* bacteria, such as *Clostridium botulinum, Clostridium butyricum* and *Clostridium beratti*. In addition, the neurotoxins used in the methods of the invention may be a botulinum toxin selected from a group of botulinum toxin types A, B, C, D, E, F, and G. In one embodiment of the invention, the neurotoxin administered to the patient is botulinum toxin type A. Botulinum toxin type A is desirable due to its high potency in humans, ready availability, and known use for the treatment of skeletal and smooth muscle disorders when locally administered by intramuscular injection. The present invention also includes the use of (a) neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants should retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Although the composition may only contain a single type of neurotoxin, such as botulinum toxin type A, as the active ingredient to suppress neurotransmission, other therapeutic compositions may include two or more types of neurotoxins, which may provide enhanced therapeutic effects of the disorders. For example, a composition administered to a patient may include botulinum toxin type A and botulinum toxin type B. Administering a single composition containing two different neurotoxins may permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the $GABA_A$ receptor. The $GABA_A$ receptor inhibits neuronal activity by effectively shunting current flow across the cell membrane. $GABA_A$ receptor modulators may enhance the inhibitory effects of the $GABA_A$ receptor and reduce electrical or chemical signal transmission from the neurons. Examples of $GABA_A$ receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat neuropsychiatric disorders may include one or more neurotoxins, such as botulinum toxins, in addition to ion channel receptor modulators that may reduce neurotransmission.

The neurotoxin may be intracranially administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a botulinum toxin within a tissue appears to be a function of dose and can be graduated. Jankovic J., et al *Therapy With Botulinum Toxin*, Marcel Dekker, Inc., (1994), page 150. Thus, diffusion of botulinum toxin can be controlled to reduce potentially undesirable side effects that may affect the patient's cognitive abilities. For example, the neurotoxin may be administered so that the neurotoxin primarily effects neural systems believed to be involved in the neuropsychiatric disorder, and does not have negatively adverse effects on other neural systems, such as primary sensory systems.

In addition, the neurotoxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of neurotoxins that may not have a functional targeting moiety (e.g., a portion of the toxin that binds to a neurotoxin receptor), and/or a translocation domain). By way of example, and not by way of limitation, a fragment of a botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its toxic effects within the cell. The pH of the target tissue is only temporarily lowered so that neuronal and/or glial injury is reduced.

Similarly, the neurotoxin may be administered intracranially, and a composition containing other pharmaceutical agents, such as antipsychotics, that can cross the blood brain barrier may be administered systemically, such as by intravenous administration, to achieve the desired therapeutic effects.

The neurotoxin may also be administered intracranially using intracranial implants. Intracranial implants have been used for various conditions. For example, stereotactically implanted, temporary, iodine-125 interstitial catheters can be used to treat malignant gliomas. Scharfen, C. O., et al., *High Activity Iodine-125 Interstitial Implant For Gliomas*, Int. J. Radiation Oncology Biol Phys 24(4);583-591:1992. Additionally, permanent, intracranial, low dose $^{125}$I seeded catheter implants have been used to treat brain tumors. Gaspar, et al., *Permanent $^{125}$I Implants for Recurrent Malignant Gliomas*, Int J Radiation Oncology Biol Phys 43(5);977-982: 1999. See also chapter 66, pages 577-580, Bellezza D., et al., *Stereotactic Interstitial Brachytherapy*, in Gildenberg P. L. et al., *Textbook of Stereotactic and Functional Neurosurgery*, McGraw-Hill (1998).

Surgically implanted biodegradable implants have been utilized to locally administer anti-cancer drugs to treat malignant gliomas. For example, polyanhydride wafers containing 3-bis(chloro-ethyl)-1-nitrosourea (BCNU) (Carmustine) have been used as intracranial implants. Brem, H. et al., *The Safety of Interstitial Chemotherapy with BCNU-Loaded Polymer Followed by Radiation Therapy in the Treatment of Newly Diagnosed Malignant Gliomas: Phase I Trial*, J Neuro-Oncology 26:111-123:1995.

A polyanhydride polymer, Gliadel® (Stolle R & D, Inc., Cincinnati, Ohio) a copolymer of poly-carboxyphenoxypropane and sebacic acid in a ratio of 20:80 has been used to make implants, and has been intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al, *Placebo-Controlled Trial of Safety and Efficacy of Intraoperative Controlled Delivery by Biodegradable Polymers of Chemotherapy for Recurrent Gliomas*, Lancet 345;1008-1012:1995.

Implants useful in practicing the methods disclosed herein may be prepared by mixing a desired amount of a stabilized neurotoxin (such as non-reconstituted BOTOX®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58;672-684:1998.

Local, intracranial delivery of a neurotoxin, such as a botulinum toxin, can provide a high, local therapeutic level of the toxin and can significantly prevent the occurrence of any systemic toxicity since many neurotoxins, such as the botulinum toxins, are too large to cross the blood brain barrier. A controlled release polymer capable of long term, local delivery of a neurotoxin to an intracranial site can circumvent the restrictions imposed by systemic toxicity and the blood brain barrier, and permit effective dosing of an intracranial target tissue. A suitable implant, as set forth in U.S. Pat. No. 6,306, 423 entitled "Neurotoxin Implant", allows the direct introduction of a chemotherapeutic agent to a brain target tissue via a controlled release polymer. The implant polymers used are preferably hydrophobic so as to protect the polymer incorporated neurotoxin from water induced decomposition until the toxin is released into the target tissue environment.

Local intracranial administration of a botulinum toxin, according to the present invention, by injection or implant to a nucleus of the brain having neurons believed to be involved in symptoms associated with neuropsychiatric disorder provides a superior alternative to systemic administration of pharmaceuticals to patients to alleviate the symptoms associated with neuropsychiatric disorders.

The target sites for administration of the neurotoxin to the patient may be targeted by using a stereotactic placement apparatus. For example, a neurotoxin containing implant, or a needle containing a neurotoxin, may be stereotactically placed at a desired target site using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three dimensional multiplanar treatment planning (STP, Fischer, Freiburg, Germany). This equipment permits planning on the basis of magnetic resonance imaging studies, merging the CT and MRI target information for clear target confirmation.

Other stereotactic systems may also be used, including for example, the Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.). The annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

Without wishing to be bound by any particular theory, a mechanism can be proposed for the therapeutic effects of a method practiced according to the present invention. Thus, a neurotoxin, such as a botulinum toxin, can inhibit neuronal exocytosis of several different CNS neurotransmitters, for example acetylcholine. It is known that cholinergic neurons are present throughout the brain. Additionally, cholinergic nuclei exist in the basal ganglia or in the basal forebrain, with projections to cerebral regions involved in emotion, behavior, and other cognitive functions. Thus, target tissues for a method within the scope of the present invention can include neurotoxin induced reversible denervation of brain cholinergic systems, such as basal nuclei or pedunculopontine nucleis. For example, injection or implantation of a neurotoxin to a cholinergic nucleus can result in (1) downregulation of dopaminergic release from target sites of cholinergic neurons due to the action of the toxin upon cholinergic terminals projecting into the ventral tegmental area from pedunculopontine nucleus; and (2) attenuation of ventral tegmental area output due to the action of the toxin upon cholinergic neurons projecting to the ventral tegmental area.

Another mechanism proposed for the present invention includes inhibition of exocytosis of nonacetylcholine neurotransmitters. For example, it is believed that once the proteolytic domain of a neurotoxin, such as a botulinum toxin, is incorporated into a neuron, the toxin inhibits release of any neurotransmitter from that neuron. Thus, the neurotoxin may be administered to nuclei containing a substantial number of dopaminergic neurons so that the neurotoxin effectively inhibits the release of dopamine from those neurons. Similarly, the neurotoxin may be administered to other nuclei such as the Raphe nuclei to inhibit serotonin exocytosis, the locus ceruleus nuclei to inhibit norepinephrine exocytosis.

The amount of a neurotoxin selected for intracranial administration to a target tissue according to the present disclosed invention can be varied based upon criteria such as the neuropsychiatric disorder being treated, its severity, the extent of brain tissue involvement or to be treated, solubility characteristics of the neurotoxin toxin chosen as well as the age, sex, weight and health of the patient. For example, the extent of the area of brain tissue influenced is believed to be proportional to the volume of neurotoxin injected, while the quantity of the suppressant effect is, for most dose ranges, believed to be proportional to the concentration of neurotoxin injected. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill).

A neurotoxin, such as a botulinum toxin, can be intracranially administered according to the present disclosed methods in amounts of between about $10^{-4}$ U/kg to about 1 U/kg. A dose of about $10^{-4}$ U/kg can result in a suppressant effect if delivered to a small nuclei. Intracranial administration of less than about $10^{-4}$ U/kg does not result in a significant or lasting therapeutic result. An intracranial dose of more than 1 U/kg of a neurotoxin, such as a botulinum toxin, can pose a significant risk of denervating other afferent or efferent neuronal systems adjacent to such nuclei. However, it is also believed that the neurons within these nuclei are not as sensitive to the neurotoxin as are neurons at the neuromuscular junction. Accordingly, administration of a neurotoxin, such as botulinum toxin, to an intracranial target tissue involved in neuropsychiatric disorders effectively reduces symptoms associated with the disorders without causing significant cognitive dysfunction. Thus, the methods of the present invention provide more selective treatment with fewer undesirable side effects than current systemic therapeutic regimes.

A preferred range for intracranial administration of a botulinum toxin, such as botulinum toxin type A, so as to achieve an tremor suppressant effect in the patient treated is from about $10^{-4}$ U/kg to about 1 U/kg. Less than about $104^2$ U/kg can result in a relatively minor, though still observable, neuropsychiatric symptom suppressant effect. A more preferred range for intracranial administration of a botulinum toxin, such as botulinum toxin type A, so as to achieve the desired effect in the patient treated is from about $10^{-3}$ U/kg to about 1 U/kg. Less than about $10^{-3}$ U/kg can result in the desired therapeutic effect being of less than the optimal or longest possible duration. A most preferred range for intracranial administration of a botulinum toxin, such as botulinum toxin type A, so as to achieve a desired tremor suppressant effect in the patient treated is from about 0.1 units to about 20 units. Intracranial administration of a botulinum toxin, such as botulinum toxin type A, in this preferred range can provide dramatic therapeutic success.

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

As set forth above, I have discovered that administration of a neurotoxin to a patient suffering from a neuropsychiatric disorder surprisingly provides effective and long lasting treatment of the neuropsychiatric disorder, and reduces the symptoms associated with the disorder. In its most preferred embodiment, the present invention is practiced by intracranial injection or implantation of botulinum toxin type A.

EXAMPLES

The following examples set forth specific methods encompassed by the present invention to treat a neuropsychiatric disorder and are not intended to limit the scope of the invention.

Example 1

Intracranial Target Tissue Localization and Methodology

Stereotactic procedures can be used for precise intracranial administration of neurotoxin in aqueous form or as an implant to desired target tissue. Thus, intracranial administration of a neurotoxin to treat a neuropsychiatric disorder can be carried out as follows.

A preliminary MRI scan of the patient can be carried out to obtain the length of the anterior commissure-posterior commissure line and its orientation to external bony landmarks. The base of the frame can then be aligned to the plane of the anterior commissure-posterior commissure line. CT guidance is used and can be supplemented with ventriculography. The posterior commissure can be visualized on 2-mm CT slices and used as a reference point to locate the target brain areas.

Physiological corroboration of target tissue localization can be by use of high and low frequency stimulation through an electrode accompanying or incorporated into the long needle syringe used. A thermistor electrode 1.6 mm in diameter with a 2 mm exposed tip can be used (Radionics, Burlington, Mass.). With electrode high frequency stimulation (75 Hz) paraesthetic responses can be elicited in the forearm and hand at 0.5-1.0 V using a Radionics lesion generator (Radionics Radiofrequency Lesion Generator Model RFG3AV). At low frequency (5 Hz) activation or disruption of tremor in the affected limb occurred at 2-3 V. With the methods of the present invention, the electrode is not used to create a lesion.

Following confirmation of target tissue localization, a neurotoxin can be injected, thereby causing a reversible, chemical denervation of the neurons of the target site. A typical injection is the desired number of units (i.e. about 0.1 to about 5 units of a botulinum toxin type A complex in about 0.1 ml to about 0.5 ml of water or saline. A low injection volume can be used to minimize toxin diffusion away from target. Typically, the inhibitory effect of neurotransmitter release can be expected to wear off within about 2-4 months. Thus, an alternate neurotoxin format, neurotoxin incorporated within a polymeric implant, can be used to provide controlled, continuous release of therapeutic amount of the toxin at the desired location over a prolonged period. (i.e. from about 1 year to about 6 years), thereby obviating the need for repeated toxin injections.

Several methods can be used for stereotactically guided injection of a neurotoxin to various intracranial targets, such as the pedunculopontine nuclei to decrease cholinergic neurotransmission, or the ventral tegmental area to decrease the release of dopamine to alleviate positive symptoms of a neuropsychiatric disorder. For example, a stereotactic magnetic resonance imaging (MRI) method relying on three-dimensional (3D) T1-weighted images for surgical planning and multiplanar T2-weighted images for direct visualization of the pedunculopontine nuclei or the ventral tegmental area, coupled with electrophysiological recording and injection guidance for unilateral or bilateral STN injection can be used. See e.g. Bejjani, B. P., et al., *Bilateral Subthalamic Stimulation for Parkinson's Disease by Using Three-Dimensional Stereotactic Magnetic Resonance Imaging and Electrophysiological Guidance*, J Neurosurg 92(4);615-25:2000.

Computer-aided atlas-based functional neurosurgery methodology can be used to accurately and precisely inject the desired neurotoxin or implant a neurotoxin controlled release implant. Such methodologies permit three-dimensional display and real-time manipulation of cerebral structures. Neurosurgical planning with mutually pre-registered multiple brain atlases in all three orthogonal orientations is therefore possible and permits increased accuracy of target definition for neurotoxin injection or implantation, reduced time of the surgical procedure by decreasing the number of tracts, and facilitates planning of more sophisticated trajectories. See e.g. Nowinski W. L. et al., *Computer-Aided Stereotactic Functional Neurosurgery Enhanced by the Use of the Multiple Brain Atlas Database*, IEEE Trans Med Imaging 19(1);62-69:2000.

Example 2

Treatment of Schizophrenia With Botulinum Toxin Type A

A 48 year old male presents with reduced motivation and interest in daily life. The patient indicates that he hears voices. The patient is monitored regularly for six months. The symptoms gradually worsen throughout the monitoring period, and the patient is diagnosed with schizophrenia. Using CAT scan or MRI assisted stereotaxis, as set forth in Example 1 above, 2 units of a botulinum toxin type A (such as BOTOX® or about 8 units of Dysport®) is injected into the pedunculopontine nucleus. The patient is discharged within 48 hours and with a few (1-7) days enjoys significant improvement of the positive symptoms of schizophrenia. The positive symptoms of schizophrenia remain significantly alleviated for between about 2 to about 6 months. For extended therapeutic relief, one or more polymeric implants incorporating a suitable quantity of a botulinum toxin type A can be placed at the target tissue site.

Example 3

Treatment of Schizophrenia With Botulinum Toxin Type B

A 68 year female previously diagnosed and treated for schizophrenia wishes to try a new therapeutic treatment. She seeks the advice of a physician who recommends botulinum toxin therapy. Using CAT scan or MRI assisted stereotaxis, as set forth in Example 1 above, from 10 to about 50 units of a botulinum toxin type B preparation (such as Neurobloc® or Innervate™) is injected into the pedunculopontine nuclei. The patient is discharged within 48 hours and with a few (1-7) days enjoys significant improvement of the positive symptoms. Her hallucinations almost completely disappear. The positive symptoms remain significantly alleviated for between about 2 to about 6 months. For extended therapeutic relief, one or more polymeric implants incorporating a suitable quantity of a botulinum toxin type B can be placed at the target tissue site.

Example 4

Treatment of Schizophrenia With Botulinum Toxin Types $C_1$-G

A female aged 71 is admitted with disorder thought patterns and suffering from auditory and visual hallucinations. From 0.1 to 100 units of a botulinum toxin type $C_1$, D, E, F or G is injected pedunculopontine nuclei to chemically denervate the excitatory cholinergic projection to the ventral tegmental area. CAT scan or MRI assisted stereotaxis, as set forth in Example 1 above, supplemented by ventriculography is used. The patient is discharged within 48 hours and with a few (1-7) days enjoys significant remission of tremors which remain significantly alleviated for between about 2 to about 6 months. For extended therapeutic relief, one or more polymeric implants incorporating a suitable quantity of a botulinum toxin type $C_1$, D, E, F or G can be placed at the target tissue site.

Example 5

Treatment of Alzheimer's Disease With Botulinum Toxin Type A

A 85 year old male who has experienced a progressive decline in mental acuity and who no longer remembers how to perform simple tasks, such as brushing teeth, or combing hair is admitted. The patient is otherwise healthy for an 85 year old. He is diagnosed with advanced Alzheimer's disease.

A suitable stereotactic frame can be applied to the head with local anesthetic and ventriculography and stereotactic MRI can be performed. The stereotactic coordinates of the anterior commissure (AC) and the posterior commissure (PC) can be determined by using the computer software in the scanner. PC based software can be used to redraw the sagittal brain maps from the Schaltenbrand and Bailey and Schaltenbrand and Wahren atlases, stretched or shrunk as needed to the AC-PC distance of the patient and ruled in stereotactic coordinates for the actual application of the frame to the patient's head. The target sites are selected, their coordinates are read off and appropriate frame settings are made. A burr hole or twist-drill hole can be made at or rostral to the coronal suture in the same sagittal plane as the target. This can facilitate plotting the physiological data used for target corroboration since the electrode trajectories traverse a single sagittal plane.

Upon microstimulation localization of the stereotactically-MRI guided recording/stimulating needle electrode to the target, a neurotoxin implant can be injected. The implant can comprise a neurotoxin, such as a of botulinum toxin type A, incorporated within biodegradable polymeric microspheres or a biodegradable pellet, either implant format containing about 20 total units (about 1 ng) of the toxin with implant characteristics of continuous release over a period of at least about four years of a therapeutic level of the toxin at point of the implant release site and for a radius of about 2-3 mm on each side of the locus ceruleus. The implant can release about 1 unit of toxin essentially immediately and further amounts of about one unit cumulatively over subsequent 2-4 months periods.

Although the patient's loss of memory does not recover fully, the psychotic symptoms the patient was exhibiting are reduced and remain substantially alleviated for between about 2 months to about 6 months per toxin injection or for between about 1 to 5 years depending upon the particular release characteristics of the implant polymer and the quantity of neurotoxin loaded therein.

Example 6

Treatment of Alzheimer's Disease With Botulinum Toxin Types B-G

The patient of example 5 above can be equivalently treated using the same protocol and approach to target the locus ceruleus with between about 1 unit and about 1000 units of a botulinum toxin type B, $C_1$, D, E, F or G in aqueous solution or in the form of a suitable neurotoxin implant. With such a treatment, the psychotic symptoms subside within 1-7 days, and remain substantially alleviated for between about 2-6 months per toxin injection or for between about 1 to 5 years depending upon the particular release characteristics of the implant polymer and the quantity of neurotoxin loaded therein.

Example 7

Treatment of Mania With Botulinum Toxin Type A

A 44 year old male is diagnosed with bipolar disorder. An implant containing botulinum toxin type A is placed in proximity to the locus ceruleus to decrease norepinephrine release. The implant can be either an aqueous solution of botulinum toxin type A incorporated within biodegradable polymeric microspheres or botulinum toxin type A biodegradable pellet, either implant format containing about 20 total units (about 1 ng) of the toxin with implant characteristics of continuous release over a period of at least about four years of a therapeutic level of the toxin at point of the implant release site and in about 2-3 mm on each side. The implant can release about 1 unit of toxin essentially immediately and further amounts of about one unit cumulatively over subsequent 2-4 months periods.

The patient's manic symptoms can subside within 1-7 days, and can remain substantially alleviated for between about 2 months to about 6 months per toxin injection or for between about 1 to 5 years depending upon the particular release characteristics of the implant polymer and the quantity of neurotoxin loaded therein. Notably, there can be significant attenuation of hallucinations. In addition, the patient has a substantially more controlled behavioral pattern.

Example 8

Treatment of Mania With Botulinum Toxin Types B-G

The patient of example 7 above can be equivalently treated using the same protocol and approach to target with between about 1 unit and about 1000 units of a botulinum toxin type B, $C_1$, D, E, F or G in aqueous solution or in the form of a suitable neurotoxin implant. With such a treatment, the symptoms can subside within 1-7 days, and can remain substantially alleviated for between about 2-6 months per toxin injection or for between about 1 to 5 years depending upon the particular release characteristics of the implant polymer and the quantity of neurotoxin loaded therein.

Example 9

Treatment of Anxiety With Botulinum Toxin Type A

A right handed, female patient age 22 presents with a history of epilepsy. Based upon MRI and a study of EEG recording, a diagnosis of temporal lobe epilepsy is made. An implant which provides about 5-50 units of a neurotoxin (such as a botulinum toxin type A) can be inserted at the anterior part of the temporal lobe, 5-6 cm from the tip of the lobe along the middle temporal gyrus with a unilateral approach to the nondominant, left hemisphere. The epileptic seizures can be substantially reduced within about 1-7 days, and can remain substantially alleviated for between about 2 months to about 6 months per toxin injection or for between about 1 to 5 years depending upon the particular release characteristics of the implant polymer and the quantity of neurotoxin loaded therein.

Example 10

Treatment of Anxiety With Botulinum Toxin Types B-G

The patient of example 9 above can be equivalently treated using the same protocol and approach to target with between about 1 unit and about 1000 units of a botulinum toxin type B, $C_1$, D, E, F or G in aqueous solution or in the form of a suitable neurotoxin implant. With such a treatment, the epileptic seizures can subside within 1-7 days, and can remain substantially alleviated for between about 2-6 months per toxin injection or for between about 1 to 5 years depending upon the particular release characteristics of the implant polymer and the quantity of neurotoxin loaded therein.

It is concluded that neurotoxin injection or implantation of a controlled release neurotoxin implant according to the methods of the present invention, with the aid of 3D MR imaging and electrophysiological guidance, can be a safe and effective therapy for patients suffering from various neuropsychiatric disorders, such as schizophrenia, dementia, or mania. Suitable patients include those who are not responsive or have become unresponsive to systemic agents utilized to treat such disorders.

An intracranial neurotoxin administration method for treating a neuropsychiatric disorder according to the invention disclosed herein has many benefits and advantages, including the following:

1. the symptoms, such as the symptoms associated with hyperactive neuronal systems of a neuropsychiatric disorder can be dramatically reduced.

2. the symptoms of a neuropsychiatric disorder can be reduced for from about two to about four months per injection of neurotoxin and for from about one year to about five years upon use of a controlled release neurotoxin implant.

3. the injected or implanted neurotoxin exerts an intracranial target tissue site specific suppression of neuronal activity.

4. the injected or implanted neurotoxin shows little or no tendency to diffuse or to be transported away from the intracranial injection or implantation site.

5. few or no significant undesirable side effects occur from intracranial injection or implantation of the neurotoxin.

6. the amount of neurotoxin injected intracranially can be considerably less than the amount of the same neurotoxin required by other routes of administration (i.e. intramuscular, intrasphincter, oral or parenteral) to achieve a comparable suppressant effect.

7. the suppressant effects of the present methods can result in the desirable side effects of greater patient mobility, a more positive attitude, and an improved quality of life.

8. high, therapeutic doses of a neurotoxin can be delivered to an intracranial target tissue over a prolonged period without systemic toxicity.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes intracranial administration methods wherein two or more neurotoxins, such as two or more botulinum toxins, are administered concurrently or consecutively. For example, botulinum toxin type A can be administered intracranially until a loss of clinical response or neutralizing antibodies develop, followed by administration of botulinum toxin type B. Furthermore, non-neurotoxin compounds can be intracranially administered prior to, concurrently with or subsequent to administration of the neurotoxin to provide adjunct effect such as enhanced or a more rapid onset of suppression before the neurotoxin, such as a botulinum toxin, begins to exert its more long lasting suppressant effect.

My invention also includes within its scope the use of a neurotoxin, such as a botulinum toxin, in the preparation of a medicament for the treatment of a neuropsychiatric disorder, by intracranial administration of the neurotoxin.

All references, articles, patents, applications and publications set forth above are incorporated herein by reference in their entireties.

Accordingly, the spirit and scope of the following claims should not be limited to the descriptions of the preferred embodiments set forth above.

I claim:

1. A method for treating a neuropsychiatric disorder, the method comprising the steps of utilizing stereotactic procedures for administering to a human patient in need thereof a therapeutically effective, non-lethal amount of a *Clostridial neurotoxin*, wherein the *Clostridial neurotoxin* is administered intracranially to a brain nucleus located at an anatomical location of the human patient selected from the group consisting of the medulla, brain stem, pons, cerebellum and cerebrum, the brain nucleus being associated with symptoms of the neuropsychiatric disorder.

2. The method of claim 1, wherein the neurotoxin is made by a bacterium selected from the group consisting of *Clostridium botulinum, Clostridium butyricum* and *Clostridium beratti*.

3. The method of claim 1, wherein the *Clostridial neurotoxin* is a botulinum toxin.

4. The method of claim 3, wherein the botulinum toxin is selected from the group consisting of botulinum toxin types A, B, $C_1$, D, E, F and G.

5. The method of claim 3, wherein the botulinum toxin is botulinum toxin type A.

6. The method of claim 3, wherein the botulinum toxin is administered in an amount of between about $10^{-3}$ U/kg to about 10 U/kg.

7. The method of claim 1, wherein the administration step further includes implantation of a botulinum toxin containing controlled release system.

8. The method of claim 1, wherein local intracranial administration restores a balance between at least two neuronal systems that release different neurotransmitters, thereby alleviating the symptom of the neuropsychiatric disorder.

9. The method of claim 1, wherein administering the *Clostridial neurotoxin* decreases a dopamine release from a dopaminergic neuron, thereby alleviating the symptom of the neuropsychiatric disorder.

10. The method of claim 1, wherein the neuropsychiatric disorder is selected from the group consisting of schizophrenia, Alzheimer's disease, mania and anxiety.

11. A method for treating a human patient suffering from a symptom of a neuropsychiatric disorder, the method comprising the steps of utilizing stereotaxic procedures to locate intracranial target tissue in the human patient, and administering to the patient a therapeutically effective amount of a botulinum toxin, wherein the botulinum toxin is administered directly to the intracranial target tissue associated with the symptom of the neuropsychiatric disorder thereby treating the symptom of the neuropsychiatric disorder, wherein the botulinum toxin is administered to an intracranial site selected from the group of intracranial sites consisting of a locus ceruleus and a ventral tegmental area and a pedunculopontine nucleus.

12. The method of claim 11, wherein the method alleviates the symptom of the neuropsychiatric disorder in the patient by decreasing hyperactive neurotransmitter release from neurons located at the intracranial target tissue.

13. The method of claim 11, wherein the botulinum toxin is selected from the group consisting of botulinum toxin types A, B, $C_1$, D, E, F and G.

14. The method of claim 11, wherein the botulinum toxin is botulinum toxin type A.

15. A method for treating a neuropsychiatric disorder, comprising the steps of determining an intracranial target site associated with the neuropsychiatric disorder in a human patient, wherein determination of the intracranial target site utilizes a stereotactic placement apparatus to locate the intracranial target site located at an anatomical location selected from the group consisting of a medulla, a brain stem, a pons, a cerebellum and a cerebrum, and administering a therapeutically effective non-lethal amount a botulinum neurotoxin by direct administration of the botulinum neurotoxin to the intracranial site, wherein administration is facilitated by direct injection of the therapeutically effective non-lethal amount a botulinum neurotoxin to the intracranial target site or by implantation of a controlled release system that controllably releases the botulinum neurotoxin to the intracranial target site.

16. The method of claim 15, wherein the botulinum toxin selected from the group consisting of botulinum toxin types A, B, $C_1$, D, E, F and G.

17. The method of claim 15, wherein the botulinum toxin is botulinum toxin type A.

18. The method of claim 15, wherein the botulinum toxin is administered in an about between about $10^{-3}$ U/kg to about 10 U/kg.

19. The method of claim 15, wherein the botulinum toxin is a botulinum toxin type B.

* * * * *

UNITED STATES PATENT AND TRADEMARK OFFICE
CERTIFICATE OF CORRECTION

| | | |
|---|---|---|
| PATENT NO. | : 7,811,587 B2 | Page 1 of 2 |
| APPLICATION NO. | : 11/749461 | |
| DATED | : October 12, 2010 | |
| INVENTOR(S) | : Stephen Donovan | |

It is certified that error appears in the above-identified patent and that said Letters Patent is hereby corrected as shown below:

Title page, Item (56), on page 2, in column 1, under "Other Publications", line 2, delete "pysiological, diagostic," and insert -- physiological, diagnostic, --, therefor.

Title page, Item (56), on page 2, in column 1, under "Other Publications", line 4, delete "Mangaed" and insert -- Managed --, therefor.

Title page, Item (56), on page 2, in column 1, under "Other Publications", line 5, delete "Diesease-" and insert -- Disease- --, therefor.

Title page, Item (56), on page 2, in column 1, under "Other Publications", line 8, delete "opthalmopathy" and insert -- ophthalmopathy --, therefor.

Title page, Item (56), on page 2, in column 1, under "Other Publications", line 20, delete "sterotactic" and insert -- stereotactic --, therefor.

Title page, Item (56), on page 2, in column 1, under "Other Publications", line 23, delete "Stereostatic" and insert -- Stereotactic --, therefor.

Title page, Item (56), on page 2, in column 1, under "Other Publications", line 25, delete "580." and insert -- 580, 1998. --, therefor.

Title page, Item (56), on page 2, in column 1, under "Other Publications", line 36, delete "saety" and insert -- safety --, therefor.

Title page, Item (56), on page 2, in column 1, under "Other Publications", line 38, delete "Aprl" and insert -- April --, therefor.

Title page, Item (56), on page 2, in column 1, under "Other Publications", line 41, delete "follwed" and insert -- followed --, therefor.

Signed and Sealed this
Nineteenth Day of April, 2011

David J. Kappos
*Director of the United States Patent and Trademark Office*

CERTIFICATE OF CORRECTION (continued)
U.S. Pat. No. 7,811,587 B2

Title page, Item (56), on page 2, in column 2, under "Other Publications", line 12, delete "Onocology" and insert -- Oncology --, therefor.

Title page, Item (56), on page 2, in column 2, under "Other Publications", line 17, delete "isofoms" and insert -- isoforms --, therefor.

Title page, Item (56), on page 2, in column 2, under "Other Publications", line 23, delete "I-Labled" and insert -- I-Labeled --, therefor.

Title page, Item (56), on page 2, in column 2, under "Other Publications", line 39, delete "stereostatic" and insert -- stereotactic --, therefor.

Title page, Item (56), on page 2, in column 2, under "Other Publications", line 44, delete "Symptons" and insert -- Symptoms --, therefor.

Title page, Item (56), on page 2, in column 2, under "Other Publications", line 63, delete "Clincal" and insert -- Clinical --, therefor.

Title page, Item (56), on page 3, in column 1, under "Other Publications", line 25, delete "Chochrane" and insert -- Cochrane --, therefor.

Title page, Item (56), on page 3, in column 2, under "Other Publications", line 2, delete "potentcy" and insert -- potency --, therefor.

In column 1, line 10, delete "herby" and insert -- hereby --, therefor.

In column 2, line 5, delete ""phenothizines," and insert -- phenothiazines, --, therefor.

In column 2, line 7, delete "butyropenones," and insert -- butyrophenones, --, therefor.

In column 9, line 61, delete "botulinum" and insert -- Botulinum --, therefor.

In column 10, line 28, delete "norepinephine." and insert -- norepinephrine. --, therefor.

In column 11, line 5, delete "botulinum" and insert -- Botulinum --, therefor.